United States Patent [19]

Webster, Jr.

[11] Patent Number: 5,916,158
[45] Date of Patent: Jun. 29, 1999

[54] SPLIT TIP ELECTRODE CATHETER

[75] Inventor: Wilton W. Webster, Jr., Baldwin Park, Calif.

[73] Assignee: Cordis Webster, Inc., Diamond Bar, Calif.

[21] Appl. No.: 08/965,694

[22] Filed: Nov. 7, 1997

Related U.S. Application Data

[62] Division of application No. 08/726,380, Oct. 4, 1996, Pat. No. 5,836,875
[60] Provisional application No. 60/005,451, Oct. 6, 1995.
[51] Int. Cl.$^6$ ..................................................... A61B 5/042
[52] U.S. Cl. ............................. 600/374; 606/41; 606/50; 607/122
[58] Field of Search .......................... 600/374; 607/122; 606/41, 50

[56] References Cited

U.S. PATENT DOCUMENTS

| | | | |
|---|---|---|---|
| 3,920,021 | 11/1975 | Hiltebrandt | 606/50 |
| 4,848,352 | 7/1989 | Pohndorf et al. | 600/374 |
| 4,960,134 | 10/1990 | Webster, Jr. | 600/374 |
| 5,383,852 | 1/1995 | Stevens-Wright | 604/95 |
| 5,398,683 | 3/1995 | Edwards et al. | 607/122 |
| 5,500,012 | 3/1996 | Brucker et al. | 607/122 |
| 5,549,108 | 8/1996 | Edwards et al. | 128/642 |

FOREIGN PATENT DOCUMENTS 571797  12/1983  European Pat. Off. ............... 607/122

*Primary Examiner*—Lee Cohen
*Attorney, Agent, or Firm*—Christie, Parker & Hale, LLP

[57] ABSTRACT

An electrode catheter for cardiac electrophysiology. An elongated body suitable for intravascular insertion surrounds a plurality of electrode lead wires. A composite electrode comprises a plurality of tip electrodes and defines a margin along a proximal edge. Each tip electrode is electrically connected to an associated electrode lead wire and is adjacent to another tip electrode on at least one side along an axis of the elongated body. Each tip electrode is separated from the another tip electrode by insulation. A cup electrode is electrically connected to an associated electrode lead wire and defines a cavity shaped to overlap the margin of the composite electrode. The cup electrode is fixedly secured to the composite electrode and to a distal end of the elongated body and is separated from the composite electrode by insulation.

16 Claims, 5 Drawing Sheets

SPLIT TIP ELECTRODE CATHETER

CROSS-REFERENCE TO RELATED APPLICATIONS

This application is a divisional of U.S. application Ser. No. 08/726,380, filed Oct. 4, 1996, allowed, now U.S. Pat. No. 5,836,875, which is based on Provisional Application Serial No. 60/005,451 filed Oct. 6, 1995.

FIELD OF THE INVENTION

This invention relates to an electrophysiology catheter having a split tip electrode and more specifically, to an electrophysiology catheter having a split tip electrode comprising a plurality of symmetrical electrodes.

BACKGROUND OF THE INVENTION

Electrophysiology is a specialty within the field of cardiology for the diagnosis and treatment of electrical abnormalities of the heart. Diagnosis is performed using electrode-bearing catheters placed within the heart chambers. Electrodes are positioned along the catheter shaft in a primarily two-dimensional array. Electrode elements are also spaced laterally around the catheter shaft give the array a limited third dimension which is limited because of the small catheter shaft diameter.

Cardiac electrical abnormalities are typically diagnosed by detecting the course of electrical activation paths along the endocardial surfaces of the heart chambers over time. Typically, several catheters are placed within one or more heart chambers to get a "picture" of the electrical activity. Sometimes, this electrical activity is cyclical, that is, it repeats fairly well from heartbeat to heartbeat. In such cases, one catheter can serve to perform the diagnosis by moving the electrodes to various regions and comparing point-by-point activation times with a reference. This reference can be an external electrocardiogram (EKG) or another electrode catheter maintained in a stable position within the heart chamber. However, certain types of electrical activity within a heart chamber are not cyclical. Examples include atrial flutter or atrial fibrillation, and ventricular tachycardia originating in scars in the walls of the ventricle that have resulted from infarcts. Such electrical activity is cyclical, that is, it is random from heartbeat to heartbeat. To analyze or "map" this type of electrical activity, the "picture" must be obtained during one heartbeat. In other words, all the points of the map or picture must be obtained simultaneously within one-tenth of a second.

One manner of treating these forms of acyclic electrical activities is by destroying the causative heart tissue through radio frequency (RF) catheter ablation. The procedure involves ablating accessory electrical pathways in the heart using an electrophysiology catheter. The catheter is guided through a vein or artery into the patient's heart and positioned at the site of the causative accessory pathway. The catheter transmits RF energy from an external source into the accessory pathway in an amount sufficient to destroy the tissue. The ablated tissue is replaced with scar tissue which interrupts the accessory pathway and restores the normal conduction of electrical activity in the heart.

Prior to ablation, the site of the accessory pathway must be ascertained using a diagnostic or mapping catheter typically composed of electrodes for stimulating and electrodes for sensing electrical activity. The procedure involves introducing a mapping catheter into the appropriate heart chamber where the arrhythmia condition exists. The heart tissue is stimulated in a manner intended to induce the arrhythmia and expose the abnormal electrical conduction. The resulting information enables an electrophysiologist to determine the appropriate course of treatment. The evaluation generally involves multiple tests to diagnose the arrhythmia and to assess the potential effectiveness of various treatment strategies. Once the heart tissue has been successfully mapped, the mapping catheter is removed and replaced with an ablation catheter at the treatment site. RF energy is then applied at the treatment site to ablate the accessory pathway.

An example of an electrophysiology catheter is shown in U.S. Pat. No. 4,365,639 to Goldreyer wherein is shown an electrode system for a cardiac pacemaker including a stimulating electrode at the distal end of the catheter and sensing electrodes on the catheter spaced away from the stimulating electrode. The sensing electrodes are circumferentially equidistant from the stimulating electrode. A problem with this catheter is that there is only one stimulating electrode at the distal end of the catheter for stimulating heart tissue ailment. Stimulating multiple areas in the heart requires a repositioning of the catheter.

Some electrophysiology catheters can function as both a mapping catheter and an ablation catheter. Typically, a catheter of this construction comprises a plurality of electrodes placed on the distal end of the catheter and a singular distal tip electrode. Some electrodes are used for mapping while the distal tip electrode is usually used for ablation. A drawback to this construction is that the electrophysiologist cannot use the distal tip electrode as a mapping electrode. Additionally, if the electrophysiologist uses the tip electrode as a mapping electrode, fine detailed mapping of the heart where the distal tip is in contact cannot occur because the tip is a singular electrode.

What is needed is a catheter having a plurality of electrodes at its distal end capable of stimulating and sensing cardiac electrical activity in multiple areas of the heart without requiring repositioning. What is also needed is an electrophysiology catheter able to maximize the efficacy of cardiac mapping by providing a plurality of electrodes at the distal end of the catheter for determining the direction of electrical activity. What is also needed is an electrode catheter for performing electrograms, pacing, stimulation and impedance measurement, preferably with the same catheter as for ablation and mapping.

SUMMARY OF THE INVENTION

The present invention enables the above problems to be overcome and provides a split tip electrode catheter.

An embodiment of the present invention is an electrode catheter for cardiac electrophysiology. The electrode catheter comprises an elongated body suitable for intravascular insertion surrounding a plurality of electrode lead wires. A composite electrode is provided at the distal tip of the catheter which comprises a plurality of tip electrodes and defines a margin along a proximal edge. Each tip electrode is electrically connected to an associated electrode lead wire and is adjacent to another tip electrode on at least one side along an axis of the catheter's elongated body. Each tip electrode is separated from the another tip electrode by insulation. A cup electrode is electrically connected to an associated electrode lead wire and defines a cavity shaped to overlap the margin of the composite electrode. The cup electrode is fixedly secured to the composite electrode and to a distal end of the elongated body and is separated from the composite electrode by insulation.

An embodiment of the present invention is also a split tip electrode comprising a composite tip comprising a plurality of electrodes. Each electrode has a pair of flat sides meeting at an angle and an outer contact surface abutting the pair of flat sides. Each flat side of each electrode is adjacent to a flat side of another electrode and is separated therefrom by insulation. The split tip electrode further comprises means for securing the composite tip to a tubular catheter body. The securing means surrounds a plurality of electrode lead wires each of which is electrically connected to an associated electrode.

A method of using the present invention is also detailed wherein a catheter with a plurality of tip electrodes is introduced into the heart to map the heart and to locate accessory pathways. The plurality of tip electrodes allows for fine detailed mapping of the heart using the distal tip electrodes. Once the distal tip of the catheter is centered on an accessory pathway, radio frequency energy is applied to the plurality of tip electrodes for a sufficient amount of time to ablate the pathway.

Still other embodiments of the present invention will become readily apparent to those skilled in the art from the following detailed description wherein is shown and described only embodiments of the invention by way of illustration of the best modes contemplated for carrying out the invention. As will be realized, the invention is capable of other and different embodiments and its several details are capable of modification in various obvious respects, all without departing from the spirit and the scope of the present invention. Accordingly, the drawings and the detailed description are to be regarded as illustrative in nature and not as restrictive.

DETAILED DESCRIPTION

Figure 1:
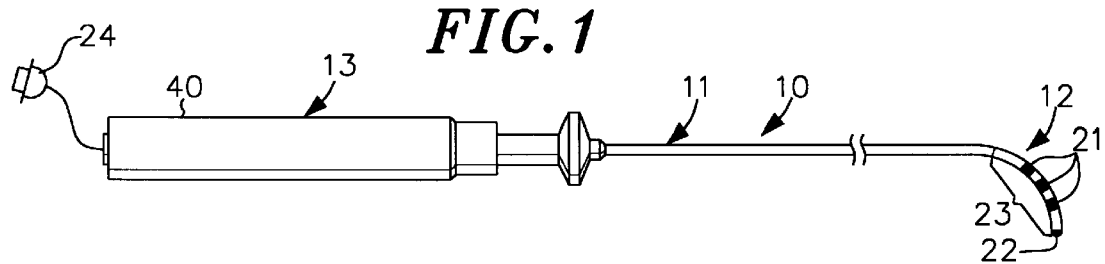
FIG. 1 is a plan view of a preferred embodiment of a split tip electrode catheter constructed in accordance with the present invention.

A preferred embodiment of a split tip electrode catheter constructed in accordance with the present invention is shown in FIG. 1. The split tip electrode catheter 10 comprises an elongated catheter body 11 having proximal and distal ends, a catheter tip 12 at the distal end of the catheter body 11 and a control handle 13 at the proximal end of the catheter body 11. The components comprising the present invention will now be discussed.

I. Catheter Body

A cross-sectional view of the junction of the catheter body 11 and the catheter tip 12 is shown in FIG. 2. The catheter body 11 comprises an elongated, tubular section forming a central lumen 15. The catheter body 11 is flexible but substantially non-compressible along its longitudinal length. The catheter body 11 can be of any construction suitable for intravascular insertion and made of any flexible and electrically insulating material. In the described embodiment, a nylon tube surrounded by one or more reinforcing layers of braided stainless steel or similar materials with a polyurethane coating is preferred, such as described in U.S. Pat. No. 5,057,092 the subject of which is hereby incorporated by reference.

The catheter body 11 surrounds a plurality of electrode lead wires 19 and a puller wire 20, both of which extend from the control handle 13 through the length of the catheter body 11 (inside the central lumen 15) and into the catheter tip 12. In the described embodiment, each of the lead wires 19 are preferably constructed of #38 copper wire having a diameter of about 0.004 inches. Also, the puller wire 20 is preferably constructed of stainless steel surrounded by a teflon sheath 25 or the like for lubricity and for keeping the puller wire 20 generally coaxial with the catheter body 11, such as described in U.S. Pat. Nos. 4,960,134 and RE34,502, the subjects of which are hereby incorporated by reference.

The length and diameter of the catheter body 11 are not critical and can vary according to the application. For the electrode catheter shown in the accompanying drawings, a length of about 40 to about 48 inches, an outer diameter of about 0.065 to about 0.100 inches (about 5 to 8 French) and an inner diameter ("lumen") of about 0.030 to about 0.040 inches are preferred.

II. Control Handle

Referring back to FIG. 1, the control handle 13 comprises a generally cylindrical housing 40 having open chambers at each end. The housing is generally symmetrical about its longitudinal axis which allows the control handle to be freely rotated without altering convenience or quality of control. The catheter body 11 is fixedly attached to the control handle 13 through one of the open chambers at one end of the control handle 13 and a molded multi-pin connector 24 is electrically connected to the control handle 13 at its other end. The control handle 13 can be plugged directly into a simulator, recorder or other electrical device. Alternatively, the connector 24 can be connected to the female end of a floating extension cable which in turn has connectors at its opposite end which can be plugged into the electrical device.

Any suitable control handle 13 which can control the longitudinal movement of the puller wire (further described hereinbelow) relative to the catheter body 11 can be used. A preferred control handle and a preferred manner of fixedly attaching the catheter body 11 to the catheter body 11, mounting the puller wire 20 and connecting the electrode lead wires 19 are described in U.S. Pat. Nos. 4,960,134, and RE34,502 the subjects of which are hereby incorporated by reference.

III. Catheter Tip

As also shown in FIG. 1, the catheter tip 12 comprises a steerable section 23, a plurality of ring electrodes 21 and a split tip electrode 22. The components comprising the catheter tip will now be discussed.

A. Steerable Section

Referring back to FIG. 2, the steerable section 23 of the catheter tip 12 comprises a short section of flexible tubing 16 forming a pair of nonoverlapping, side-by-side lumens, upper lumen 17 and lower lumen 18. These lumens are longitudinally situated off-axis and are not coaxial with the catheter tip 12. The flexible tubing 16 can be made of any suitable material and is preferably more flexible than the catheter body. In the described embodiment, the preferred material is polyurethane having a D55 hardness, such as described in U.S. Pat. Nos. 5,057,092, 4,960,134, and RE34,502, the subjects of which are hereby incorporated by reference.

The diameter of the catheter tip 12 is not critical but is preferably about the same as, or slightly smaller than, the diameter of the catheter body 11. Likewise, the length of the catheter tip 12 is not critical. In the described embodiment, the length of the catheter tip 12 is about two inches.

A pair of safety wires 48 (shown in FIG. 2A) and 49 (shown in FIG. 3) are used to secure the split tip electrode 22 to the catheter tip 12. In the described embodiment, each of the safety wires 48 and 49 are preferably constructed of Monel 400 wire having a diameter of about 0.0065 inches.

Figure 2A:
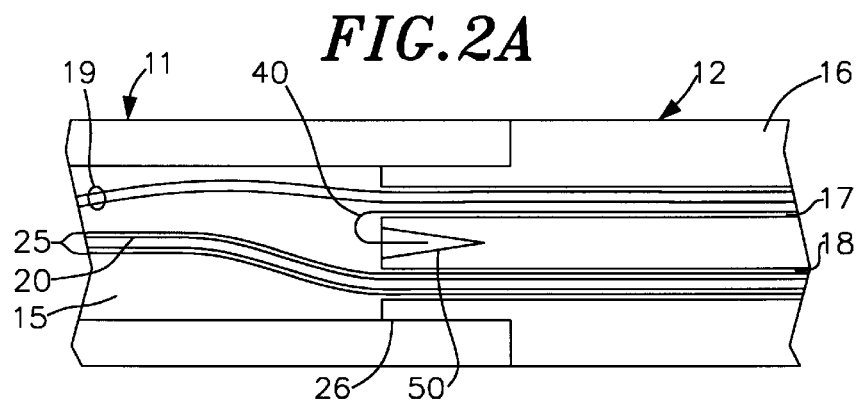
FIG. 2A is a cross-sectional view of the junction of the catheter body and the catheter tip.

A preferred means for attaching the catheter tip 12 to the catheter body 11 is shown in also shown in FIG. 2A. The proximal end of the catheter tip 12 comprises an outer circumfrential notch 26 sized to allow the notched proximal end of the catheter tip 12 to be snugly inserted into the distal end of the catheter body 11 and fixedly attached by glue or the like. The circumfrential notch 26 can additionally be tapered (not shown) at the proximal end to allow for easier insertion into the distal end of the catheter body 11. The central lumen 15 of the catheter body 11 is in communication with both upper lumen 17 and lower lumen 18 of the catheter tip 12. In the described embodiment, the upper lumen 17 encircles the electrode lead wires 19 and the safety wire 48. The lower lumen 18 encircles the puller wire 20.

Figure 2B:
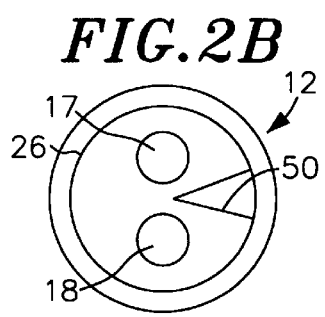
FIG. 2B is a rear view of the proximal end of the catheter tip.

A rear view of the proximal end of the catheter tip 12 is shown in FIG. 2B. A groove 50 is formed to run axially along one surface of the circumfrential notch 26 for securing the safety wire 48. The groove 50 is situated equidistant between the upper lumen 17 and lower lumen 18 and tapers upwards in the longitudinal direction away from the proximal end of catheter tip 12. The length of the groove 50 must be less than the width of the circumfrential notch 26. The safety wire 48 (see FIG. 2A) extends all the way through the catheter tip 12 from the split tip electrode 22. At the proximal end of the flexible tubing 16, the safety wire 48 is bent backwards and fit into the groove 50. The safety wire 48 is securely fixed into place when the notched proximal end of the catheter tip 12 is inserted into the distal end of catheter body 11. In the described embodiment, the groove 50 is about 0.080 inches long.

The catheter tip 12 is steerable by means of the puller wire 20 which is fixedly attached at its proximal end to the control handle 13 and at its distal end to the flexible tubing 16. By extending the puller wire 20 through the lower lumen 18, the puller wire 20 is positioned eccentrically to the axis of the catheter body 11 and thereby enables the electrode catheter to be steered. Rearward movement of the puller wire 20 in the proximal direction (relative to the catheter body 11) by manipulation of the control handle 13 results in a curving of the catheter body 11. Such curving can be used to steer the electrode catheter during cardiac electrophysiology. An example of such a puller wire construction is disclosed in U.S. Pat. Nos. 4,960,134 and RE34,502, the subjects of which are hereby incorporated by reference.

Figure 3:
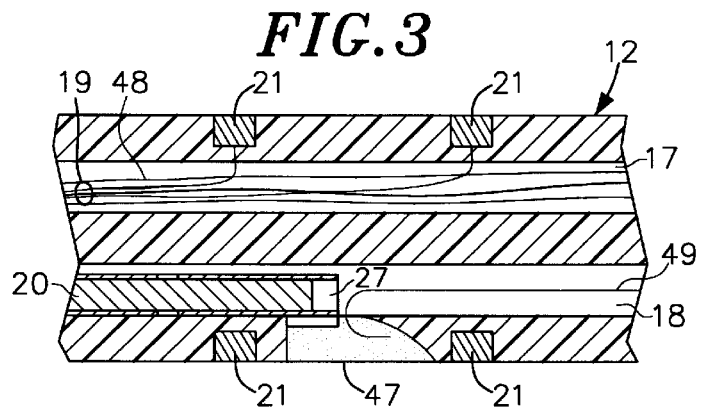
FIG. 3 is a cross-sectional view of a means of attaching the puller wire and safety wire to the wall of the catheter tip.

A preferred means for attaching the puller wire 20 and the safety wire 49 to the wall of the catheter tip 12 is shown in the cross-sectional view of FIG. 3. A crossbar 27 is fitted over and fixedly secured to the distal end of the puller wire 20. The safety wire 49 is bent backwards. Both the crossbar 27 and the safety wire 49 are situated within a notch 47 in the wall of the flexible tubing 16 which extends into the lower lumen 18 and are positioned to avoid electrical contact with each other. The crossbar 27 is larger than the opening and cannot be pulled through the opening formed by the notch 47. The portion of the notch 47 not filled by the crossbar 27 and the safety wire 49 are filled with glue or the like, preferably a polyurethane glue harder than the material of the flexible tubing 16. Rough edges, if any, of the crossbar 27 and the safety wire 49 are polished to provide a smooth, continuous surface with the outer surface of flexible tubing 16. In the described embodiment, the crossbar 27 is constructed from stainless steel and is crimped to the puller wire 20 by any conventional technique, such as described in U.S. Pat. Nos. 4,960,134 and RE34,502, the subjects of which are hereby incorporated by reference. Preferably, the crossbar 27 has a crosspiece about 0.020 inches wide and a stem about 0.030 inches long.

B. Ring Electrodes

Referring back to FIG. 1, along the length of the flexible tubing 16, there are a plurality of ring electrodes 21. Each of the ring electrodes 21 are in the form of a ring with an outer diameter of about the same as the outer diameter of the flexible tubing 16 so that a smooth, continuous surface is formed with the outer surface of the flexible tubing 16. In the described embodiment, each ring electrode has an outer diameter of about 6½ French and is preferably constructed from platinum. Each ring electrode 21 is electrically connected (as shown in FIG. 3) to one of the electrode lead wires 19 by any conventional technique.

C. Split Tip Electrode

Figure 4:
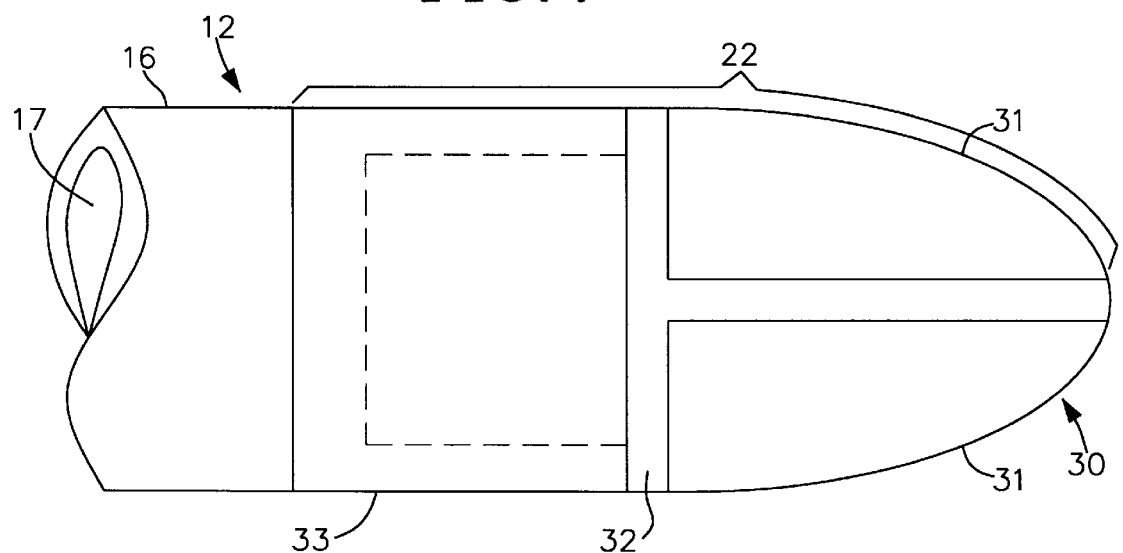
FIG. 4 is a side view of a split tip electrode constructed in accordance with the present invention.
Figure 5:
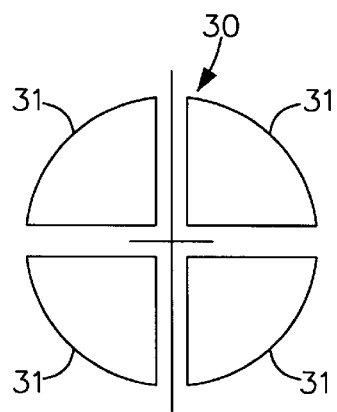
FIG. 5 is a front view of the composite tip.
Figure 6:
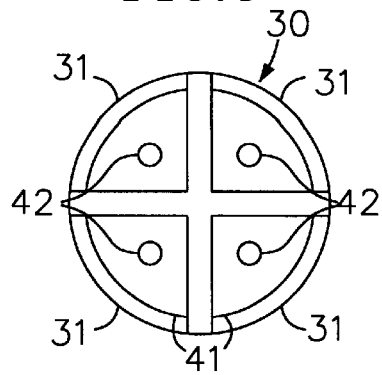
FIG. 6 is a rear view of the composite tip.
Figure 7:
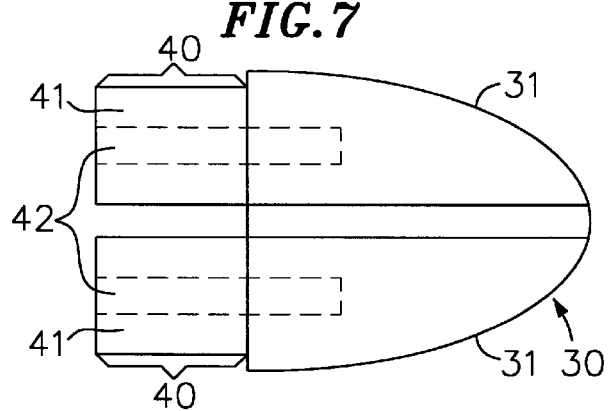
FIG. 7 is a side view of the composite tip.
Figure 8:
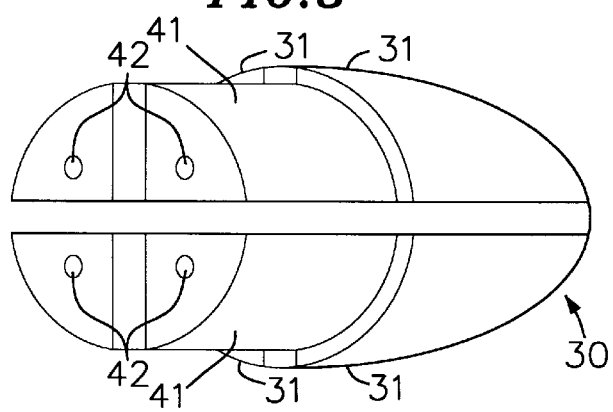
FIG. 8 is a rear perspective view of the composite tip.
Figure 9:
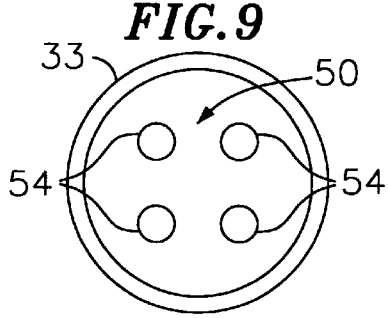
FIG. 9 is a front view of the cup electrode.
Figure 10:
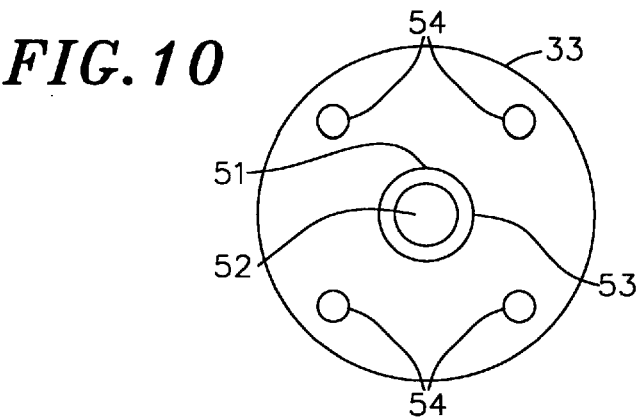
FIG. 10 is a rear view of the cup electrode.
Figure 11:
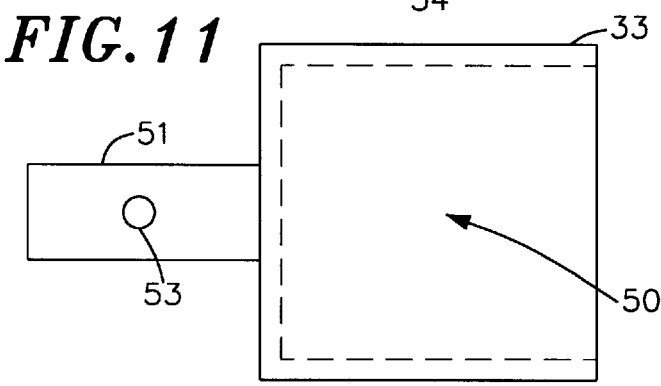
FIG. 11 is a side view of the cup electrode.
Figure 12:
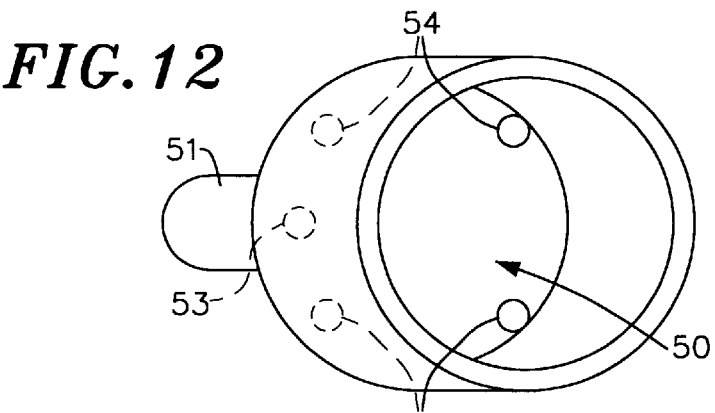
FIG. 12 is a front perspective view of the cup electrode.
Figure 13:
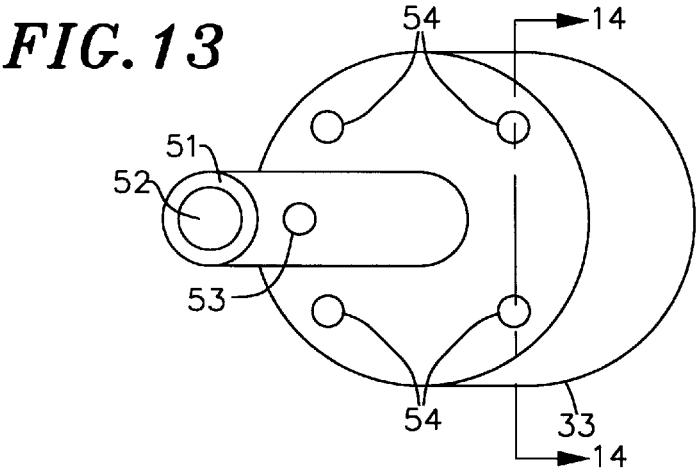
FIG. 13 is a rear perspective view of the cup electrode.

The split tip electrode 22 is mounted on the distal end of the catheter tip 12. As shown in the side view of FIG. 4, the split tip electrode 22 comprises a composite electrode 30 and a cup electrode 33. The composite electrode 30 comprises a plurality of tip electrodes 31 forming a series of quadrant electrodes. Each of the tip electrodes 31 are electrically attached by any conventional technique to an associated electrode lead wire 19 as further described hereinbelow. Each of the tip electrodes 31 and the cup electrode 33 are separated from each other by insulation 32 which in the described embodiment is preferably cured liquid polyurethane.

The composite electrode 30 is shown in FIGS. 5, 6, 7 and 8 in respectively front, rear, side and rear perspective views. The insulation 32 has been omitted from these figures for clarity. Each tip electrode 31 is preferably symmetrical and has a pair of flat sides preferably meeting at a right angle and an outer contact surface abutting the pair of flat sides. The tip electrodes 31 are arranged with each of their respective flat sides adjacent to the flat side of another electrode. To facilitate the connection of the electrode lead wires 19, an electrode lead bore 42 is formed in the proximal end of each tip electrode.

The composite electrode 30 is secured to the cup electrode 33 on a margin 40 along the proximal edge of each of the tip electrodes 31. Preferably, each tip electrode 31 has a recessed surface 41 defining the margin 40. The outer contact surfaces of the tip electrodes 31 are fashioned so that the composite electrode 30 has a bullet shape with a rounded tip.

Each of the tip electrodes 31 can be of any suitable construction and are preferably made of platinum or alloys of platinum and iridium. The various dimensions of each of the tip electrodes is not critical so long as the combination of the individual tip electrodes forming the composite electrode 30 fit within the cup electrode 33 along the margin 40.

A presently preferred construction comprises modifying a 7FR tip electrode, part no. 5203-07, manufactured by Cordis Webster Inc., Baldwin Park, Calif. The tip electrode is machined to the preferred outer dimensions (described further hereinbelow), the electrode lead bores are drilled into its proximal end and the tip electrode is cut into four tip electrodes. A preferred overall length is about 0.120 inches with a margin 40 of about 0.040 inches. A preferred overall diameter is about 0.092 +0.001 or −0.002 inches. Each electrode lead bore 42 is preferably about 0.016 inches in diameter and about 0.055 inches deep. The axis of each electrode lead bore 42 is about 0.0382 inches from the axis of the composite electrode 30. The preferred depth of the recessed surface 41 is about 0.0085 inches.

A preferred method of constructing the composite electrode 30 is by machining the 7FR tip electrode to a desired bullet shape with a rounded tip and having an overall length of about 0.210 ±0.010 inches, a diameter of about 0.092 +0.001 or −0.002 inches, a contact surface length of about 0.080 inches and a margin of about 0.040 inches wide and of about 0.0085 inches deep. The remaining 0.090 inches on the proximal end is fashioned into a stem with a diameter of about 0.033±0.001 inches. The stem is removed during a later part of the manufacturing process. Four electrode lead bores 42 are drilled into the proximal end of the 7FR tip electrode and the machined part is placed in a holder. The part is then cut into four equal segments with a 0.004 inch wire EDM (electrical discharge machining) tool. These segments comprise the tip electrodes 31. The segments are ultrasonically cleaned and liquid polyurethane is applied to secure the four pieces together, thereby forming the composite tip 30. The part is then cured at 75° C. for a suitable amount of time and post-cured for one hour at 100° C. A number 24 WW collet is used to remove the cured composite electrode 30 from the holder and the stem is cut off and the distal face of the composite electrode 30 made flush.

The cup electrode 33 is shown in FIGS. 9, 10, 11, 12 and 13 in respectively front, rear, side, front perspective and rear perspective views. The cup electrode 33 defines a cavity 50 shaped to overlap the margin 40 along the proximal edge of the composite electrode 30 so that the cup electrode 33 and composite electrode 30 form a smooth continuous surface with the outer surface of the catheter tip 12. The cup electrode 33 is separated from the composite electrode 30 by insulation 32.

Figure 14:
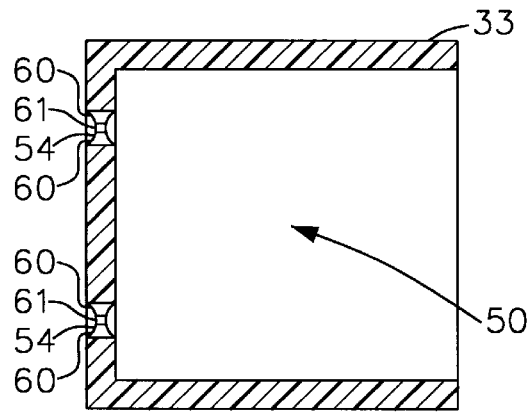
FIG. 14 is a cutaway view of the cup electrode taken along the line 14—14 in FIG. 13.

The cup electrode 33 further comprises a stem 51 formed on a proximal end of the cup electrode 33 axially aligned with the catheter tip 12. The stem 51 is preferably cylindrical in shape with an axial bore 52 and has an orifice 53 extending into the axial bore 52. The cup electrode 33 also further comprises a plurality of pass-through bores 54 for allowing the electrode lead wires 19 for the composite electrode 30 to pass through when the split tip electrode 22 is fully assembled. Each of the pass-through bores 54 are parallel to the axis of the catheter tip 12, axially aligned with an associated electrode lead bore 42, and equally spaced along the proximal end of the cup electrode 33. To insulate the cup electrode 33 from the composite electrode 30, each of the pass-through bores 54 have a meniscus insulator 60 that defines a hole 61 through which an electrode lead wire passes through, as shown in the cutaway view of the cup electrode 33 in FIG. 14. The meniscus insulator 60 prevents each electrode lead wire 19 from electrically contacting the cup electrode 33.

Figure 15:
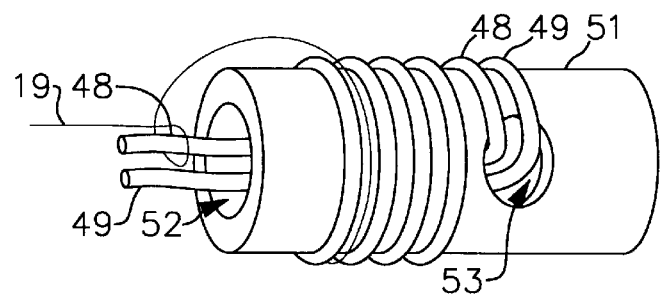
FIG. 15 is a rear perspective view of the cup electrode with the safety wires and the electrode lead wire attached.

The pair of safety wires 48 and 49 and an electrode lead wire 19 and are fixedly attached to the stem 51 of the cup electrode 33. A rear perspective view of the cup electrode 33 with the safety wires 48 and 49 and the electrode lead wire 19 attached is shown in FIG. 15. Each of the safety wires 48 and 49 are inserted into the axial bore 52 and passed back out through the orifice 53. The safety wires 48 and 49 are then wrapped about two or three times around the stem 51. An electrode lead wire 19 is wrapped once around either of the safety wires and is then wrapped about two or three times around the stem 51 between the pair of safety wires 48 and 49 in a direction opposite from the safety wires. The electrode lead wire 19 and safety wires 48 and 49 are fixedly secured into place, preferably by soldering as in the described embodiment.

The cup electrode 33 can be of any suitable construction and is preferably made of platinum or alloys of platinum and iridium. Similarly, the dimensions of the cup electrode are not critical. A presently preferred construction uses the same aforementioned 7FR tip electrode machined to the desired dimensions. The preferred length of the cup electrode 33 is about 0.130 inches with a contact surface of about 0.080 inches. The preferred depth of the cavity 50 is about 0.060 inches and the preferred outer diameter about 0.092 inches with a cavity diameter of about 0.078 inches. The preferred outer diameter of the stem 51 is about 0.033±0.001 inches with an axial bore diameter of about 0.020±0.002 inches. The pass-through bores preferably have a diameter of about 0.018 inches located at 45° angles from each other and are at a distance of about 0.0382 inches from the axis of the catheter body 11.

The preferred method of constructing the cup electrode 33 is as follows. First, the 7FR tip electrode is machined to the appropriate dimensions. The four pass-through bores 54 are filled with liquid polyurethane to form a concave meniscus in each. The cup electrode 33 is then cured at 375° F. for a suitable amount of time. A hole 61 of about 0.008 to 0.010 inches in diameter is formed in each meniscus. The pair of safety wires 48 and 49 are inserted into and through the stem 51 and wrapped around it. The electrode lead wire 19 is wrapped around one of the safety wires and wrapped around the stem 51 as described above. The safety wires and electrode lead wire are soldered onto the stem 51. In the described embodiment, the preferred solder comprises a composition of about 25% indium, 2% silver and 73% tin. A soldering flux, such as Stay Clean flux, is applied. The completed cup electrode 33 is ultrasonically defluxed in 70% isopropyl alcohol.

Figure 16:
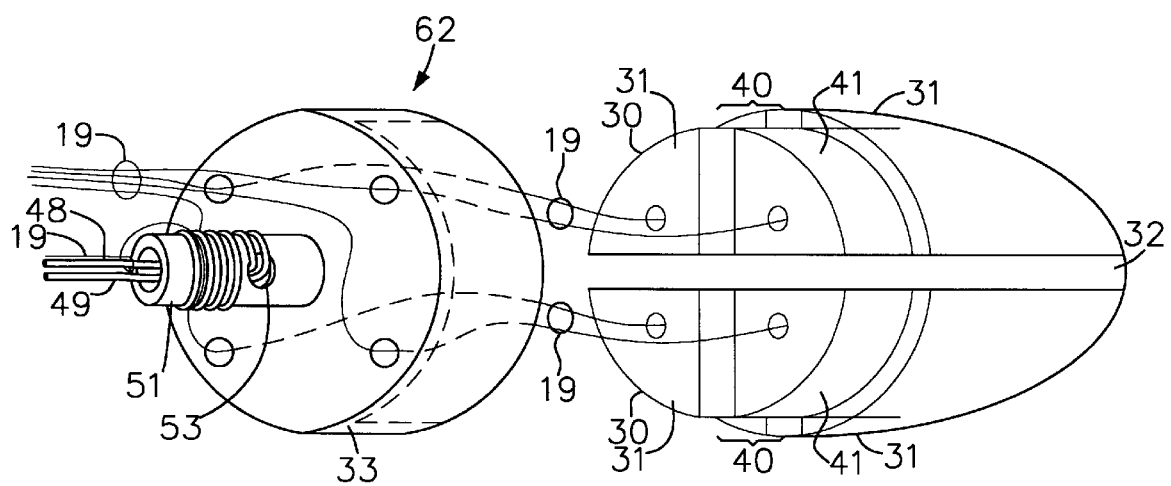
FIG. 16 is an exploded isometric view showing the assembly of the composite tip and the cup electrode.

An exploded isometric view of the assembly of the composite electrode 30 and the cup electrode 33 into the split tip electrode 22 is shown in FIG. 16. The four associated electrode lead wires 19 for each of the tip electrodes 31 are fed through the holes 61 in the meniscus insulators 60 of the cup electrode 33. Each electrode lead wire 19 is then fixedly attached to a tip electrode 31 by any conventional technique. In the described embodiment, each electrode lead wire 19 is soldered using a solder comprising a composition of one part 96/4 solder and 1 part 52 indium/48 solder at a temperature of about 400° F. The completed composite electrode 30 is ultrasonically defluxed in 70% isopropyl alcohol.

To complete assembly, the insulation 32, preferably liquid polyurethane insulation, is applied to the margin 40 and the distal end of the composite electrode 30. The composite electrode 30 is inserted into the cup electrode 33 and a finishing coat of insulation is applied, which is again preferably liquid polyurethane insulation. The completed split tip electrode 62 is cured at 375° F. for a suitable amount of time. Excess insulation is removed and the entire tip polished.

The split tip electrode 62 is fixedly attached to the distal end of the catheter tip 12, preferably by glue or similar material. A preferred means for attaching is described in U.S. Pat. No. 4,960,134, reissued Patent No. RE34,502, to Webster, Jr., the subject of which is hereby incorporated by reference.

In practice, the present invention is ideal for mapping the heart and ablating accessory pathways causing arrhythmias. To perform this function, the electrophysiologist inserts the distal tip of the catheter into a vein or artery and advances the tip into the heart. The heart is then mapped by using each of the plurality of tip electrodes, the cup electrode and any ring electrodes on the catheter. Once an accessory pathway has been found, the electrophysiologist places the distal tip of the catheter adjacent to the pathway. By using the plurality of tip electrodes and the cup electrode, the electrophysiologist can confirm that the distal tip is located directly adjacent to the pathway. The electrophysiologist then applies radio frequency energy to the plurality of tip electrodes and the cup electrode. The close spacing of the tip electrodes and the cup electrode allows for all of these electrodes to function as one continuous ablation electrode, because the lesion created by the radio frequency applied will be continuous.

The preceding description has been presented with references to presently preferred embodiments of the invention as shown in the drawings. Persons skilled in the art and technology to which this invention pertains will appreciate that alterations and changes in the described structures can be practiced without meaningfully departing from the principle, spirit and scope of this invention Accordingly, the foregoing description should not be read as pertaining only to the precise structures described and shown in the accompanying drawings, but rather should be read as consistent with and as support for the following claims which are to have their fullest and fairest scope.

What is claimed is:

1. A split tip electrode comprising:
a composite tip electrode having a longitudinal axis, a distal section comprising an external surface and a proximal section that forms a recessed stem, said composite tip electrode comprising a plurality of electrode members positioned about the longitudinal axis of the composite tip electrode, each electrode member forming a portion of the distal section and a portion of the proximal section and having at least one interior flat surface and an exterior contact surface, wherein each interior flat surface of each electrode member is adjacent to a flat surface of another electrode member and electrically isolated therefrom by a non-conductive material; and
means for securing the composite tip electrode to a tubular catheter body, the securing means comprising a rigid cylindrical side wall in surrounding relation to at least a portion of the stem of the composite tip electrode.

2. A split tip electrode according to claim 1, wherein the composite tip electrode comprises four electrode members, each forming a quadrant of the composite tip electrode.

3. A split tip electrode according to claim 1, wherein each of the electrode members comprises an electrode lead bore at its proximal end for receiving an electrode lead wire.

4. A split tip electrode according to claim 1, wherein each electrode member has a pie-shaped cross-sectional configuration.

5. A split tip electrode comprising:
a composite tip electrode having a distal section comprising an external surface and proximal and distal ends and a proximal section that forms a recessed stem, said composite tip electrode comprising a plurality of electrode members electrically isolated from each other; and
a securing electrode spaced proximally from the proximal end of the distal section of the composite electrode, said securing electrode comprising a generally cylindrical side wall that forms a ring electrode and a hollow interior that receives and fixedly secures at least a portion of the stem of the composite electrode, said securing electrode being electrically isolated from the composite tip electrode.

6. A split tip electrode according to claim 5, wherein the securing electrode further comprises a recessed stem formed on a proximal end of the securing electrode.

7. A split tip electrode according to claim 5, wherein the composite tip electrode has a longitudinal axis and the plurality of electrode members are positioned about the longitudinal axis of the composite tip electrode, each electrode member forming a portion of the distal section and a portion of the proximal section and having at least one interior flat surface and an exterior contact surface, wherein each interior flat surface of each electrode member is adjacent to a flat surface of another electrode member and electrically isolated therefrom by a non-conductive material.

8. A split tip electrode according to claim 5, wherein the composite tip electrode comprises four electrode members, each forming a quadrant of the composite tip electrode.

9. A split tip electrode according to claim 5, wherein each electrode member has a pie-shaped cross-sectional configuration.

10. A split tip electrode comprising:
a composite tip electrode having a distal section comprising an external surface and proximal and distal ends and a proximal section that forms a recessed stem, said composite tip electrode comprising a plurality of electrode members electrically isolated from each other; and
a cup electrode spaced proximally from the proximal end of the distal section of the composite electrode, said cup electrode comprising a generally cylindrical side wall having proximal and distal ends that forms a ring electrode, a base wall fixedly attached to the proximal end of the side wall, and a hollow interior formed by the side and base walls that receives and fixedly secures at least a portion of the stem of the composite electrode, said cup electrode being electrically isolated from the composite tip electrode.

11. A split tip electrode according to claim 10, wherein the cup electrode further comprises a recessed stem at its proximal end.

12. A split tip electrode according to claim 11, wherein the stem of the cup electrode is cylindrical and comprises an axial bore and a transverse orifice extending through the side of the stem to meet the axial bore.

13. A split tip electrode according to claim 10, wherein the cup electrode defines a proximal end comprising a plurality of pass-through bores, each bore comprising a meniscus insulator with a hole defined therethrough.

14. A split tip electrode according to claim 10, wherein the plurality of electrode members are positioned about the axis of the composite tip electrode, each electrode member having a pair of interior flat sides and an exterior contact surface, wherein each interior flat side of each electrode member is adjacent to a flat side of another electrode member and electrically isolated therefrom by a non-conductive material.

15. A split tip electrode according to claim 10, wherein the composite tip electrode comprises four electrode members, each forming a quadrant of the composite tip electrode.

16. A split tip electrode according to claim 10, wherein each electrode member has a pie-shaped cross-sectional configuration.

* * * * *